United States Patent [19]
Kelly et al.

[11] Patent Number: 5,133,812
[45] Date of Patent: Jul. 28, 1992

[54] CORROSION RESISTANT CUTTING TOOL AND METHOD OF MANUFACTURE

[75] Inventors: John S. Kelly, Arcadia; Jonel Cera, Corona, both of Calif.

[73] Assignees: Minnesota Mining and Manufacturing Company, St. Paul, Minn.; E.T.M. Corporation, Monrovia, Calif.

[21] Appl. No.: 647,556

[22] Filed: Jan. 29, 1991

[51] Int. Cl.⁵ .............................................. C21D 9/18
[52] U.S. Cl. ..................... 148/528; 148/426;
148/325; 148/327; 148/333; 148/334; 148/522;
219/77; 219/85.22; 228/262.13; 228/182;
228/231; 30/134; 30/142; 30/143
[58] Field of Search ............... 148/12 E, 12 EA, 127,
148/12.4, 426, 325, 327, 333, 334; 219/77,
85.22; 228/121, 263.13, 194, 182, 263.15, 231,
162; 30/134, 142, 143

[56] References Cited

U.S. PATENT DOCUMENTS

| | | | |
|---|---|---|---|
| 3,167,423 | 1/1965 | Johnson, Jr. | 75/126 |
| 4,148,973 | 4/1979 | Sexton et al. | 428/680 |
| 4,150,978 | 4/1979 | Schlatter et al. | 75/126 C |
| 4,745,037 | 5/1988 | DeCristofaro et al. | 148/403 |

OTHER PUBLICATIONS

N. DeCristofaro and C. Henschel, "Metglas Brazing Foil", Welding Journal, Jul. 1978 pp. 33-38.
Data Sheet, Lescalloy BG42 vim-var High Performance Bearing Steel (1987).
Process Certificate for Job No. 10713A (Sep. 12, 1990).

Primary Examiner—R. Dean
Assistant Examiner—Sikyin Ip
Attorney, Agent, or Firm—Pretty, Schroeder, Brueggemann & Clark

[57] ABSTRACT

A completely corrosion resistant, high strength cutting tool such as an orthodontic wire cutter includes a stainless steel body having a pair of corrosion resistant alloy steel bonding tips brazed thereto. The tips are brazed to the body using a nickel alloy brazing foil at a brazing temperature of approximately 1900 degrees F. After a rough grinding to appropriate shape, the entire tool is heat treated in a process that heats the tool to an austenitizing temperature for the cutting tips that is about 2050 degrees F. and substantially above the brazing temperature to achieve a tip hardness of 62-67 Rc. Thereafter finish grinding, buffing, polishing and honing of the cutting edges completes the manufacture of the cutting tool.

30 Claims, 1 Drawing Sheet

CORROSION RESISTANT CUTTING TOOL AND METHOD OF MANUFACTURE

BACKGROUND OF THE INVENTION

Orthodontics requires a precision wire cutter tool when installing appliances on teeth. The tool must be compact, reasonably lightweight, strong, capable of exact placement under difficult conditions and sharp enough to cut stainless steel wire with a minimal controlling force. Because of the harsh environment provided by sterilization procedures such as autoclave and chemiclave the tool should also be corrosion resistant. While orthodontic wire cutting tools have become quite sophisticated, they have been unable to meet all of these objectives.

A typical orthodontic wire cutting tool is shaped much like a pair of pliers except that the pinching fingers each carry a facing cutter blade that squeezes and cuts a wire strand between them. Experimentation has shown that the cutting blades or tips should have a hardness between 62 and 67 on the Rockwell c (Rc) hardness scale. If too soft, the cutting edge too readily deforms and looses its sharpness. If too hard, the edge becomes brittle and subject to early fracture.

To achieve an economical combination of cutting tip hardness and tool body handle strength, it has become common practice to make the cutter body from a high grade stainless steel such as type 420 or 425M stainless steel. A relatively hard T15 tool steel cobalt chromium alloy formed into a small, frangible planar cutting tip was then heat treated and subsequently brazed to the body of the cutter tool. The tool with hardened tips in place was then rough ground, the frangible tip web was broken and a finishing grind, buffing and polishing was performed. Final precision assembly to attain proper tightness in the pivot action was accomplished and the cutting tips or blades were sharpened with a diamond hone.

While the cutting tool thus manufactured in accordance with a conventional process is a high quality, precision tool, it has two significant disadvantages. The T15 tool steel used for the cutting tips is subject to corrosion from stringent sterilization procedures like autoclave and chemiclave. This corrosion is conventionally controlled by plating the finished cutter first with nickel and then with chromium. Not only does this plating process increase the cost of the cutting tool, but it is not completely effective. As the tool is used the protective plating quickly wears away along the cutting edge and the cutting tips begin to corrode.

In addition, in order to avoid tempering the hardened T15 tool steel tips as they are brazed to the cutter body, a low temperature foil brazing medium must be used to effect the braze. For this purpose a low temperature silver alloy brazing foil is used to enable a brazing temperature of about 1500 degrees F.

While the low temperature brazing foil preserves the hardness of the cutting tips, it is difficult to get the foil to properly wet the bonding surfaces. As a result a failure rate of the braze joint on the order of 2-3% has been found to occur during use. Even higher failure rates have been encountered when cutting heavy gauge wire.

SUMMARY OF THE INVENTION

A high precision, high strength corrosion resistant cutting tool and method of manufacture in accordance with the invention includes a stainless steel body having a receiving surface and a corrosion resistant alloy bearing steel frangible cutting tip blank brazed to the tool body using a nickel alloy foil brazing medium having a brazing temperature of approximately 1900 degrees F.

After brazing, a rough grinding operation shapes the cutting tool while the cutting tip is relatively soft. The frangible web of the cutting tip is then broken to establish two cutting edges in facing relationship along the break.

The entire cutting tool is then subjected to heat treatment for the cutting tips in a vacuum furnace. Even though only the cutting tips, representing a small portion of the tool, require the heat treatment, the entire tool is heat treated. The tool is heated to an austenitizing temperature of 2050 degrees F. for the tip material and maintained at temperature for 30 minutes. Surprisingly, this heating to a temperature 150 degrees F. above the brazing temperature does not damage the brazed joints. They retain a strength and reliability that is superior to the lower temperature silver alloy foil brazed joints that have been previously used. After air cooling to $-100$ degrees F. for two hours and two tempering heats the tool cutting tip has been hardened to a range of 62–67 Rc and is ready for finish grinding, buffing and polishing.

The cutting tool is then finally assembled with the pivot screw being precisely shimmed to provide a controlled tightness at the pivot point that will assure that precise alignment will be maintained between the cutting blades without making the joint so tight that undue force is required to open and close the tool. The facing cutting edges are then sharpened in a diamond honing operation.

Because both the stainless steel body and the alloy steel cutting tips are corrosion resistant, it is not necessary to implement the nickel plating and chromium plating steps required for conventional cutting tools. Further, because corrosion resistance is inherent in the materials of the cutting tips and stainless steel body, corrosion cannot be induced as a result of wear that inevitably occurs during use of the tool.

BRIEF DESCRIPTION OF THE DRAWINGS

A better understanding of the invention may be bad from a consideration of the following Detailed Description, taken in conjunction with the accompanying drawings in which.

DETAILED DESCRIPTION OF THE INVENTION

Figure 1:
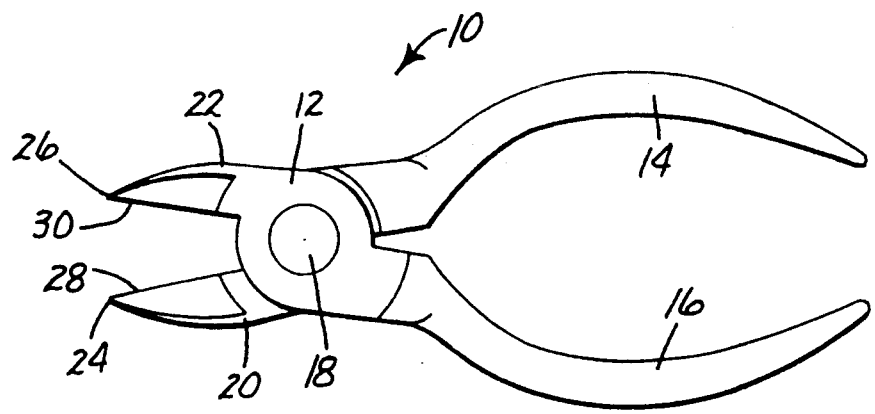
FIG. 1 is a top view of a corrosion resistant wire cutting tool in accordance with the invention.

Referring now to FIG. 1, a high precision, high strength, corrosion resistant wire cutting tool 10 in accordance with the invention includes a body having two handle sections 14, 16 held in pivotable relationship by a pivot screw 18. The two handle sections 14, 16 have respectively two integral jaw or fingers 20, 22 extending on an opposite side of pivot screw 18 from handle sections 14, 16. Each of the fingers 20, 22 has bonded to a bottom side thereof a generally planar cutting tip 24, 26 of corrosion resistant, high performance bearing steel with a hardness in the range of 62-67 on the Rockwell c hardness scale.

Facing, mating sharpened cutting edges 28, 30 are defined on the respective steel cutting tips 24, 26. Upon placing a wire strand (not shown) between the two cutting edges 28, 30 and squeezing the handles 14, 16 together, the cutting edges 28, 30 are correspondingly squeezed into contact with each other until the wire strand is cut.

Figure 2:
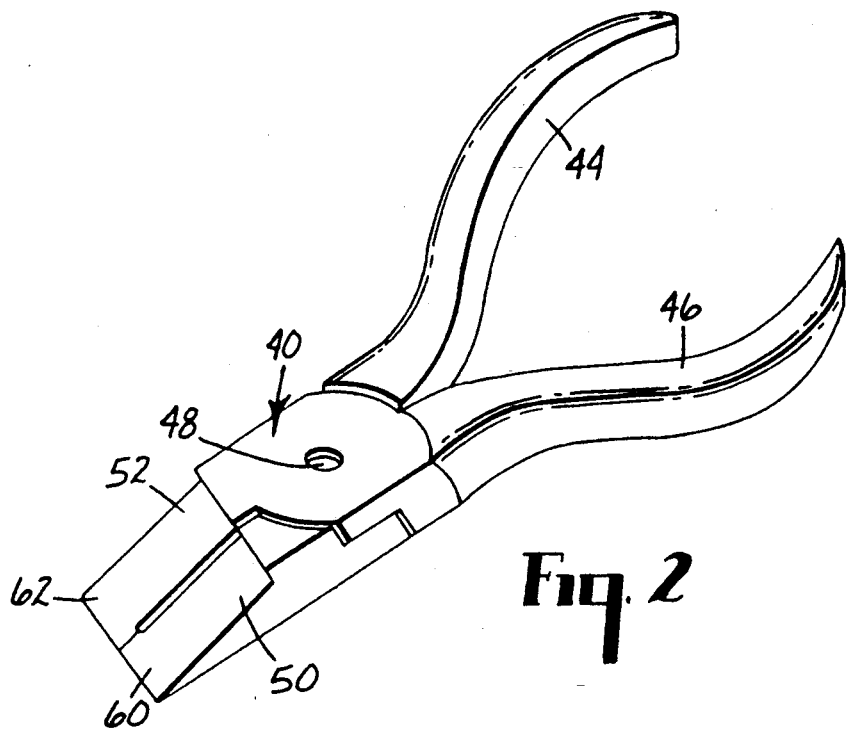
FIG. 2 is a perspective view of a wire cutting tool body in accordance with the invention and generally shows a bottom side.
Figure 3:
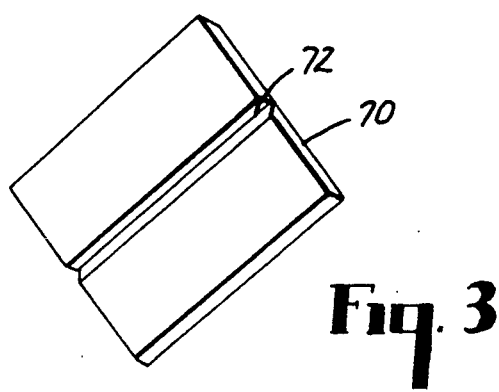
FIG. 3 is a perspective view of a corrosion resistant frangible web cutting tip web adapted to be brazed to the tool body shown in FIG 1.

Referring now to FIG. 2, there is shown a rough cutting tool body 40 having handle sections 44, 46 corresponding to handle sections 14, 16 of cutting tool 10. Handle Sections 44, 46 are maintained in pivotal relationship by a pivot screw 48. Body 40 has fingers 50, 52 connected to and extending on an opposite side of pivot screw 48 from respective handle sections 44, 46. A planar receiving surface having sections 60, 62 is defined on fingers 50, 52 to receive a frangible cutting tip web 70 shown in FIG. 3.

Cutting tip web 70 has a longitudinally extending V groove or break line 72 centrally located along planar web 70. Web 70 is thus constructed to be frangible so that it may be selectively broken along the break point 72 to form the facing cutting blade edges 28, 30 as shown in FIG. 1.

Tool body 40 is made of a high quality stainless steel such as type 420 or 425M. The cutting tip planar web member 70 is made of a high performance, corrosion resistant alloy steel such as the Lescalloy BG42 vim-var bearing steel manufactured by Latrobe Steel Company. This steel alloy has a composition including by weight 1.15% carbon, 0.30% silicon, 0.50% manganese, 14.50% chromium, 4.00% molybdenum, and 1.20% vanadium. This steel alloy is further described in U.S. Pat. Nos. 3,167,423 and 4,150,978 which are hereby incorporated by reference.

The corrosion resistant, frangible steel cutting tip web member 70 is brazed to the receiving surfaces 60, 62 using a nickel alloy brazing foil as a brazing medium. In one preferred example, the foil is a 2.25 mil thick foil consisting of, by weight percent, 0.02% carbon, 4.25% silicon, less than 0.02% phosphorus, less than 0.02% sulfur, 7.05% chromium, 3.09% boron, 2.89% iron, 0.09% cobalt, 0.01% titanium, 0.01% aluminum, 0.02% zirconium, balance nickel. Such material is commercially available from the Metglas Division of Allied Signal, Inc. The corrosion resistant cutting tip web 70 is brazed to receiving surfaces 60, 62 in a conventional brazing process by heating the tip of body 40, the brazing foil and the cutting tip member 70 to a temperature of approximately 1900 degrees F. under vacuum in a magnetic induction heater. The brazing is accomplished with the cutting tip web 70 clamped to the receiving surfaces 60, 62 with the foil sandwiched between the web 70 and the receiving surfaces 60, 62.

After vacuum cooling to a nonoxidizing temperature, the body 40 with brazed soldered tip 70 is rough ground to form the approximate final product shape as shown for cutting tool 10 in FIG. 1. Because the alloy steel cutting tips 70 have not yet been hardened, the rough grinding process is somewhat easier than that for prior processes wherein the cutting tips were hardened prior to brazing and rough grinding.

Upon completion of the rough grinding process, web member 70 was broken along fracture line 72 in a breaking press to separate web member 70 into its two separate cutting tip sections 24, 26. After breaking frangible web 70 the entire cutting tool 10 is placed on a suitable rack and inserted into a vacuum furnace for the purpose of heat treating the alloy tips 24, 26 to produce a hardness in the range of 62-67 Rc. The hardness is typically tested at four different points distributed along the cutting edge.

In a preferred heat treating process, the cutting tool 10 was preheated in a vacuum oven to a temperature of 1500 degrees F. It took 15 minutes to reach the preheat temperature which was then maintained for 30 minutes. The temperature was then increased to an austenitizing temperature of 2050 degrees F. with the specified temperature being reached in 15 minutes and being maintained for 30 minutes thereafter. Following the 30 minutes at the austenitizing temperature, the cutting tool 10 was fan cooled in the atmosphere of an inert gas such as argon to near room temperature for a time of approximately 1 hour and 5 minutes.

Thereafter the cutting tool 10 was subjected to an air cool at approximately −100 degrees F. After 40 minutes the tool reached the desired temperature of −100 degrees F. and was thereafter maintained at temperature for a period of 2 hours.

Subsequent to cooling, the tool 10 was tempered at 975 degrees F., requiring approximately 30 minutes to reach temperature, being maintained at the temperature for 2 hours and subsequently being air cooled to room temperature. The tool 10 with cutting tips 24, 26 was then subjected to a second tempering heat to a temperature of 975 degrees F., requiring 30 minutes to reach the desired temperature, being maintained at the temperature for 2 hours, and then being air cooled.

The above heat treating process was found to produce in the alloy steel corrosion resistant cutting tips 24, 26 a hardness in the desired range of 62-67 Rc. This hardness has been found by experimentation to be sufficient to withstand long term wire cutting operation while maintaining durability without introducing a brittleness that produces fracturing of cutting edges during use. The heat treating process did not produce separation of the brazed joints even though the maximum temperature was 150 degrees F. higher than the brazing temperature.

Following heat treatment, the wire cutting tool 10 was subjected to a finish grinding operation, buffed and polished to provide a smooth, shiny appearance. Thereafter the handle sections 14, 16 were finally assembled in a conventional process by inserting and tightening the pivot screw 18 with shims selected to provide a carefully controlled tightness in the pivot joint. Manufacture of the wire cutting tool 10 was then completed by sharpening the cutting edges 24, 26 in a diamond honing process. Because all portions of the cutting tool 10 are inherently corrosion resistant and made of corrosion resistant material, the additional nickel and chrome plating steps required by prior processes are not required for the improved wire cutting tool 10. As a result, corrosion cannot be induced by a wearing away of any corrosion protection plating during extended use. The entire cutting tool remains corrosion resistant even in the environment of sterilization procedures when used for orthodontic application. In addition, the nickel foil brazing medium was found to provide a high strength bond of the alloy steel cutting tip web 70 to the body 40 to virtually eliminate the bonding failures which have been found to occur with prior silver alloy brazing media.

Although there has been shown and described herein a corrosion resistant, high strength wire cutting tool in accordance with the invention for the purpose of enabling a person of ordinary skill in the art to make and use the invention, it will be appreciated that the invention is not limited thereto. Accordingly, any modifications, variations or equivalent arrangements within the scope of the attached claims should be considered to be within the scope of the invention.

What is claimed is:

1. A method of manufacturing a cutting tool comprising the steps of:
   forming a stainless steel cutting tool body having a receiving surface for matingly receiving a cutting tip;
   brazing a corrosion resistant alloy steel cutting tip containing chromium, molybdenum and vanadium to the receiving surface using as a brazing medium a nickel alloy, the brazing being accomplished by heating the receiving surface, cutting tip and brazing medium to a brazing temperature that is sufficient to melt the brazing medium and braze the cutting tip to the receiving surface; and then
   heat treating the cutting tool subsequent to the brazing step with a treatment that heats the cutting tool to a temperature in excess of the brazing temperature to produce a hardness in the cutting tip in a range of 62–67 on the Rockwell c hardness scale.

2. A method of manufacturing according to claim 1 wherein the brazing temperature is approximately 1900 degrees F. and the maximum heat treatment temperature is approximately 2050 degrees F.

3. A method of manufacture according to claim 1 wherein the tip is made of a high performance bearing steel alloy.

4. A method of manufacturing according to claim 1 wherein the cutting tool is a hand held wire cutter.

5. A method of manufacturing according to claim wherein the body is composed of a type 420 stainless steel.

6. A method of manufacturing according to claim wherein the body is composed of a type 425M stainless steel.

7. A method of manufacturing according to wherein the tip is composed of a bearing steel including substantially by weight percent the following materials:
   1.15% carbon
   0.30% silicon
   0.50% manganese
   14.50% chromium
   4.00% molybdenum
   1.20 % vanadium 8. A method of manufacturing according to claim 1 wherein the brazing medium has substantially the following composition by weight percentage:
   0.02% carbon
   4.25% silicon
   less than 0.02% phosphorus
   less than 0.02% sulfur
   7.05% chromium
   3.09% boron
   2.89% iron
   0.09% cobalt
   0.01% titanium
   0.01% aluminum
   0.02% zirconium
   Balance nickel 9. A method of manufacturing according to claim 1 wherein the heat treating step includes in order the following steps:
   preheat in a vacuum furnace 30 minutes at 1500 degrees F.;
   austenitizing in a vacuum furnace for 30 minutes at 2050 degrees F.;
   inert gas fan cool to an inactive temperature;
   air cool to −100 degrees F. and remain at temperature 2 hours;
   temper 2 hours at 975 degrees F.;
   air cool;
   temper 2 hours at 975 degrees F.; and
   air cool.

10. A method of manufacturing according to claim 9 wherein the brazing temperature is substantially 1900 degrees F.

11. A method of manufacturing according to claim 10 wherein the body comprises type 420 stainless steel.

12. A method of manufacturing according to claim 10 wherein the body comprises type 424M stainless steel.

13. A method of manufacturing a cutting tool having a stainless steel body and a corrosion resistant alloy steel cutting tip containing chromium, molybdenum, and vanadium secured to the body, the method comprising the steps of:
   brazing the corrosion resistant alloy steel cutting tip to the stainless steel body using a nickel alloy brazing foil containing silicon, chromium, boron and iron at a selected brazing temperature; and then
   heat treating the body and cutting tip subsequent to the brazing step by heating the body and cutting tip to an austenitizing temperature greater than the brazing temperature to produce a cutting tip hardness in a range of 62–67 on a Rockwell c hardness scale.

14. A method of manufacturing a fully corrosion resistant cutting tool from a stainless steel body and a cutting tip blank consisting of a corrosion resistant alloy steel containing chromium, molybdenum and vanadium, the method comprising the steps of:
   brazing the cutting tip blank to the stainless steel body at a brazing temperature using a nickel alloy brazing foil;
   rough grinding the body and cutting tip blank to a desired shape after the brazing step to form a rough ground cutting tool having a cutting tip formed from the cutting tip blank;
   heat treating the rough ground cutting tool after the rough grinding step to produce a cutting tip hardness in a range of 62–67 on the Rockwell c hardness scale, the heat treating including heating the rough ground cutting tool to an austenitizing temperature for the cutting tip that is in excess of the brazing temperature;
   finish grinding the rough ground cutting tool; and
   diamond honing the cutting tip of the corrosion resistant cutting tool to form a cutting edge.

15. A method of manufacturing according to claim 14 wherein the brazing temperature is substantially 1900 degrees F. and the austenitizing temperature is substantially 2050 degrees F.

16. A method of manufacturing according to claim 15 wherein the cutting tip blank is frangible along a break line and further comprising the step between the rough grinding and heat treating steps of breaking the cutting tip blank along the break line to define a pair of opposed cutting edges on opposite sides of the break.

17. A method of manufacturing a cutting tool comprising:
   forming a cutting tool body from a stainless steel;
   forming a cutting tool tip from a corrosion resistant tool steel;
   brazing the cutting tip to the tool body using a nickel brazing medium at a brazing temperature;
   heat treating the cutting tool subsequent to the brazing operation with a heat treatment that heats the cutting tool to a temperature in excess of the brazing temperature; and
   forming a cutting edge on the cutting tip after heat treating the cutting tool.

18. A method of manufacturing according to claim 17 wherein the corrosion resistant steel of the cutting tip includes chromium, molybdenum and vanadium.

19. A method of manufacturing according to claim 17 wherein the corrosion resistant tool steel consists substantially by weight percentage of:
   1.15% = carbon
   0.30% = silicon
   0.50% = manganese
   14.50% = chromium
   4.00% = molybdenum
   1.20 % = vanadium
   Balance = iron 20. A method of manufacturing according to claim 17 wherein the selected brazing medium used in the brazing step is a nickel alloy.

21. A method of manufacturing according to claim 17 further comprising the step of heat treating the cutting tip after brazing the cutting tip to the tool body.

22. A method of manufacturing according to claim 17 wherein the heat treating includes raising the temperature of the cutting tip and tool body to an austenitizing temperature that is greater than the brazing temperature used to braze the cutting tip to the tool body.

23. A method of manufacturing according to claim 22 wherein a maximum temperature for the heat treating is at least 150 degrees F. greater than a maximum brazing temperature.

24. A method of manufacturing according to claim 22 wherein the heat treating operation includes a heat treating that provides the cutting tip with a final hardness in a range of 62-67 on a Rockwell c hardness scale.

25. A cutting tool having all parts thereof made of corrosion resistant material comprising:
   a stainless steel body having a receiving surface defined thereon; and
   at least one corrosion resistant alloy steel tip containing chromium, molybdenum and vanadium secured to the receiving surface by brazing at a brazing temperature using a nickel alloy brazing foil containing silicon, chromium, boron and iron, the stainless steel body with at least one alloy steel cutting tip brazed to the receiving surface thereof being subjected to a heat treatment including heating to an austenitizing temperature for the at least one tip that is in excess of the brazing temperature to produce a cutting tip hardness in a range of 62-67 on the Rockwell c hardness scale.

26. A cutting tool according to claim 25 wherein the brazing temperature is 1900 degrees F. and the austenitizing temperature is 2050 degrees F.

27. A corrosion resistant hand held wire cutting tool comprising:
   a stainless steel body; and
   a pair of corrosion resistant alloy steel tips having a hardness in a range of 62-67 on the Rockwell c hardness scale secured by brazing to the body in mutually opposed cutting relationship and then heat treated to a temperature higher than the brazing temperature, the steel tips being secured to the body by brazing using a nickel alloy brazing material.

28. A corrosion resistant cutting tool comprising:
   a stainless steel body;
   at least one corrosion resistant alloy tool steel cutting tip, the cutting tip having a cutting edge defined thereon and having a hardness in a range of 62-67 on the Rockwell c hardness scale; and
   a nickel alloy braze joint securing the cutting tip to the stainless steel body and then heat treating the cutting tool at a temperature higher than the brazing temperature.

29. A corrosion resistant cutting tool according to claim 28 wherein the cutting tip has a hardness in the range of 62-67 on a Rockwell c hardness scale at at least four points distributed along the cutting edge.

30. A corrosion resistant cutting tool according to claim 28 wherein the alloy tool steel forming the cutting tip consists of substantially by weight percentage:
   1.15% = carbon
   0.30% = silicon
   0.50% = manganese
   14.50% = chromium
   4.00% = molybdenum
   1.20 % = vanadium
   Balance = iron

* * * * *

UNITED STATES PATENT AND TRADEMARK OFFICE
CERTIFICATE OF CORRECTION

PATENT NO. : 5,133,812

DATED : July 28, 1992

INVENTOR(S) : John S. Kelly et al.

It is certified that error appears in the above-identified patent and that said Letters Patent is hereby corrected as shown below:

column 2, line 5, change "!900" to --1900--.

column 2, line 62, change "!0" to --10--.

column 5, lines 39-40, change "claim wherein" to --claim 1 wherein--.

column 5, lines 42-43, change "claim wherein" to --claim 1 wherein--.

column 5, line 45, change "to wherein" to --to claim 1 wherein--.

column 6, line 21, change "424M" to --425M--.

Signed and Sealed this

Ninth Day of November, 1993

*Attest:*

BRUCE LEHMAN

*Attesting Officer*     *Commissioner of Patents and Trademarks*